United States Patent [19]

Lin et al.

[11] 4,128,639

[45] Dec. 5, 1978

[54] NITROSOUREA ANALOGS OF THYMIDINE

[75] Inventors: Tai-Shun Lin, North Haven; Paul H. Fischer, North Branford; William H. Prusoff, Branford; George T. Shiau, New Haven, all of Conn.

[73] Assignee: Research Corporation, New York, N.Y.

[21] Appl. No.: 860,453

[22] Filed: Dec. 14, 1977

[51] Int. Cl.² .................. A61K 31/70; C07H 17/00
[52] U.S. Cl. ........................................ 424/180; 536/23
[58] Field of Search .......................... 536/23, 53, 24; 424/180

[56] References Cited

U.S. PATENT DOCUMENTS

| | | | |
|---|---|---|---|
| 3,694,428 | 9/1972 | Hardegger et al. | 536/53 |
| 4,057,684 | 11/1977 | Kimura | 536/53 |

OTHER PUBLICATIONS

Chem. Abstracts, 80, 78686z (1974).
Chem. Abstracts, 85, 172500j (1976).
Chem. Abstracts, 85, 171859w (1976).

*Primary Examiner*—Johnnie R. Brown
*Assistant Examiner*—Blondel Hazel
*Attorney, Agent, or Firm*—Cooper, Dunham, Clark, Griffin & Moran

[57] ABSTRACT

Alkyl and haloalkyl nitrosourea analogs of thymidine are useful in the treatment of cancers in mice.

11 Claims, 1 Drawing Figure

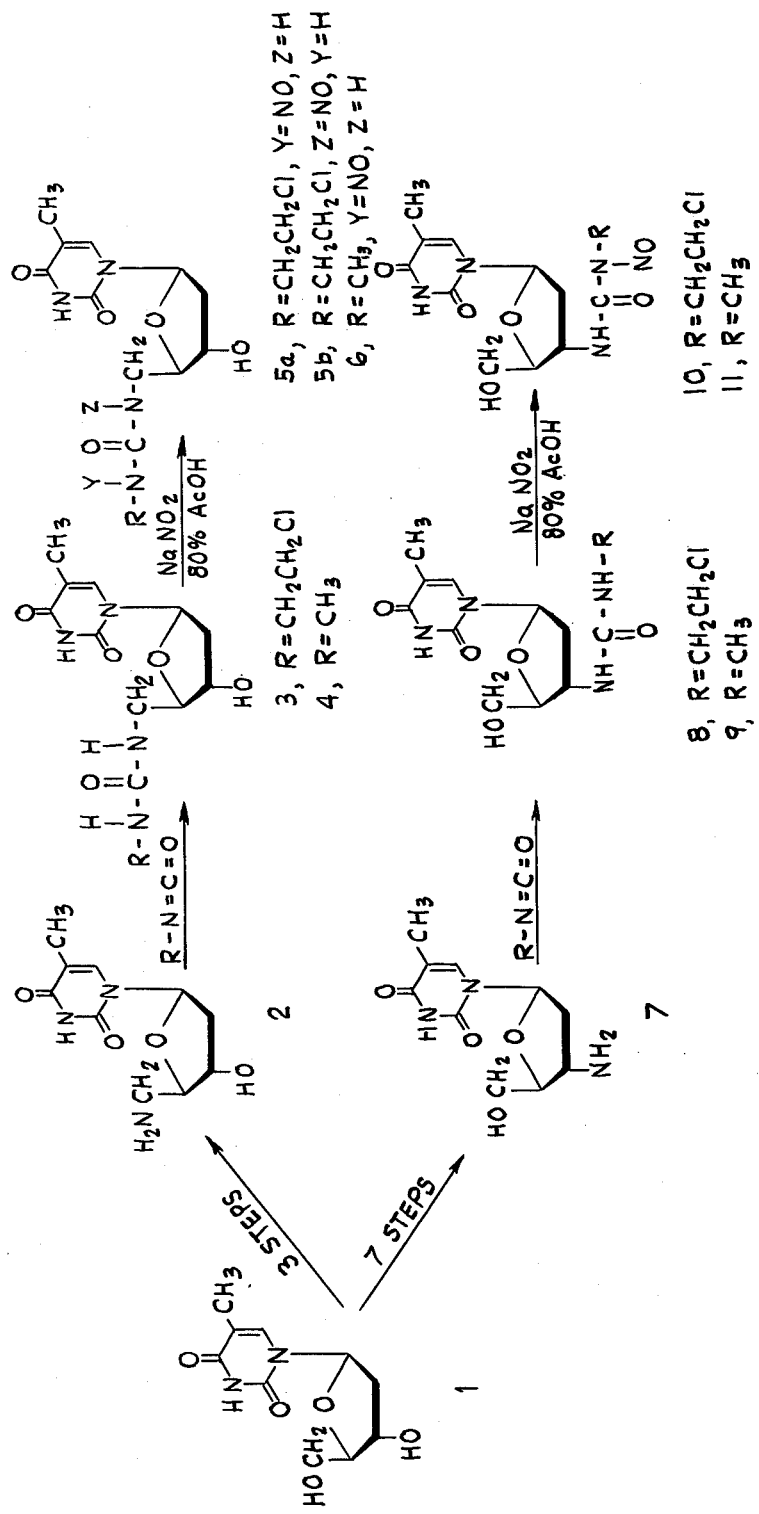

NITROSOUREA ANALOGS OF THYMIDINE

This invention is concerned with antineoplastic agents. More particularly, it is concerned with certain alkyl and haloalkyl nitrosourea analogs of thymidine. It is concerned also with certain novel intermediates useful in the production of such compounds.

The FIGURE shows the presently preferred process for the production of the nitrosourea analogs of the invention, and of the intermediates. The preparation of the compounds is illustrated in the examples.

Halogenated alkyl nitrosoureas have long been known as antineoplastic agents. The best known of the class are 1,3-bis(2-Chloroethyl)-1-nitrosourea (BCNU), 1-(2-Chloroethyl)-3-cyclohexyl-1-nitrosourea (CCNU) and 1-(2-Chloroethyl-3-(4-methylcyclohexyl)-1-nitrosourea (MeCCNU). All have been used clinically. Unfortunately, the compounds are toxic not only to neoplastic cells but also to normal cells. The most consistent organic toxicities of the drugs involve bone marrow, lymphoid tissue, kidneys, lungs, liver, and the gastrointestinal tract. The art, therefore, has long sought compounds with the useful properties of the nitrosourea drugs, but without their undesirable side effects, or at least, compounds in which the undesirable side effects can be controlled.

The compounds of this invention are potent inhibitors of the replication of L1210 leukemia cells in culture. Unexpectedly, this inhibition is reversed in the presence of pyrimidine deoxyribonucleosides. The compounds are also useful in vivo.

The therapeutically useful compounds of the invention include those represented by the formulas:

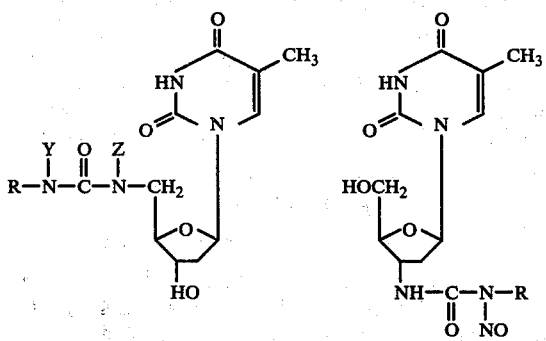

5a, R = $CH_2CH_2Cl$, Y = NO, Z = H
5b, R = $CH_2CH_2Cl$, Z = NO, Y = H           10, R = $CH_2CH_2Cl$
6, R = $CH_3$, Y = NO, Z = H                  11, R = $CH_3$

The methods of synthesizing the therapeutically active compounds are shown in the FIGURE. The known intermediates, 5'-amino-5'-deoxythymidine (2) and 3'-amino-3'-deoxythymidine (7) are prepared from thymidine in three steps and seven steps respectively according to the procedures of Horwitz (specifically cited in the examples). It was found best for the preparation of the compounds of this invention to isolate compound 7 as the free base instead of as the hydrochloride salt.

Compounds 2 and 7 are converted to the corresponding urea compounds:

(3) 5'-[3-(2-chloroethylureido)]-5'-deoxythymidine
(4) 5'-(3-methylureido)-5'-deoxythymidine
(8) 3'-[3-(2-chloroethylureido)]-3'-deoxythymidine
(9) 3'-(3-methylureido)-3'-deoxythymidine by reaction with the appropriate methyl or chloroethyl isocyanate.

Reaction is effected in a polar solvent, suitably a water alkanol mixture such as a 3:1 methanol or ethanol water mixture at a low temperature, typically −5° C. to 10° C.

Normally, the isocyanate is added to a solution of the aminodeoxythymidine with stirring at the selected temperature. It is preferred to use a slight molar excess of the isocyanate, although the amount may vary from equimolar to up to a 20% molar excess.

Often the product precipitates as it is formed. It can then be recovered by filtration. If it does not form as a solid phase, it may be recovered by evaporating the solvent in vacuo.

The final products:

(5) 5'-[3-(2-chloroethyl)-nitrosoureido]-5'-deoxythymidine
(6) 5'-(3-methyl-3-nitrosoureido)-5'-deoxythymidine
(10) 3'-[3-(2-chloroethyl)-3-nitrosoureido]-3'-deoxythymidine
(11) 3'-(3-methyl-3-nitrosoureido)-3'-deoxythymidine are prepared by reaction with nitrous acid which may be formed by reaction between an alkali metal nitrite and an organic or inorganic acid.

Reaction is effected in a polar solvent, most conveniently an aqueous acid solution, for example a lower carboxylic acid such as acetic acid, containing the organic substrate. The nitrite, for example sodium nitrite is added. Normally, an excess of nitrous acid is generated. The product which forms may be isolated in any convenient manner. For example, the excess reagents may be neutralized, the solvent evaporated at low pressure and the product purified by crystallization. Alternatively, the excess metallic ion can be removed using an ion exchange resin, and the resulting volatile products removed by evaporation at low pressure to isolate the product.

As an example of the activity of these compounds, both compounds 10 and 11 are more potent inhibitors of replication of L1210 cells in culture than BCNU. The $ED_{50}$ values of the compounds are, respectively, 1.5 μM, 1.0 μM and 4 μM.

A single intraperitoneal injection of compound 5 (150 mg/kg) produced 33% long term survivors (>60 days) and increased the life span of the dying animals 211% over the controls when given to $CDF_1$ mice 2 days after inoculation with $1 \times 10^5$ L1210 cells.

Surprisingly the cytotoxicity of the compounds of this invention is reversed when a pyrimidine deoxyribonucleoside is introduced into the neoplastic cell culture system. Table 1 shows the results of such a study with compounds 10 and 11.

TABLE 1

| REVERSAL OF CYTOTOXICITY OF NITROSOUREA ANALOGS OF THYMIDINE | | |
|---|---|---|
| | Percent Reversal | |
| Reversing Agent | Cpd. 10 | Cpd. 11 |
| Thymidine | | |
| 0 μM | 0 | 0 |
| 1 μM | 22 | 21 |
| 5 μM | 45 | 54 |
| 25 μM | 54 | 62 |
| Deoxyuridine | | |
| 0 μM | 0 | 0 |
| 1 μM | 4 | — |

TABLE 1-continued
REVERSAL OF CYTOTOXICITY OF NITROSOUREA ANALOGS OF THYMIDINE

| Reversing Agent | Percent Reversal | |
|---|---|---|
| | Cpd. 10 | Cpd. 11 |
| 5 μM | 32 | 49 |
| 25 μM | 51 | 81 |
| Deoxycytidine | | |
| 0 μM | 0 | 0 |
| 1 μM | 5 | — |
| 5 μM | 28 | 42 |
| 25 μM | 40 | 74 |
| 125 μM | — | 100 |

Concentrations of the Nitrosourea analogs of thymidine in the experiments are 5 μM.

It is expected that in normal use the selected compound will be coadministered with the selected pyrimidine deoxyribonucleoside, or within a short period before administration, so that the active compound will perform its useful function and the inhibitor will protect the normal cells. The presently preferred method of administration is parenteral The compounds of the invention may be provided and utilized in various oral dosage forms as capsules, tablets, and the like, with excepients such as starch, milk sugar or certain types of clay. They will, however, normally be employed in parenteral dosage forms, for example, in sterile aqueous media containing sufficient glucose or saline to be isotonic. Other carriers such as propylene glycol, diethyl carbonate, glycerol, sesame oil or peanut oil may also be employed.

Suitable dosage levels with the compounds of this invention will be of the order of 8 to 12 mg/kg of body weight per day. They may be administered as one dosage unit, or as two or more dosage units containing lesser amounts.

The following non-limiting examples are given by way of illustration only.

Melting points were determined with a Thomas-Hoover Unimelt apparatus and are not corrected. The uv spectra were recorded on a Beckman Model-25 spectrophotometer, the ir spectra on a Perkin-Elmer 257 instrument, and the NMR spectra on a Bruker 270 HX spectrometer at 270 MHz. TLC and preparative TLC were performed on Eastman 6060 precoated silica gel sheets with fluorescent indicator and on Analtech silica gel GF plates, using CHCl$_3$-EtOH (4:1 v/v) and CHCl$_3$-EtOH (3:1 v/v) solvent systems respectively. Elemental analyses were carried out by Baron Consulting Co., Analytical Services, Orange, CT. Where analyses are indicated only by symbols of the elements, the analytical results obtained for those elements were within +0.4% of the theoretical values.

EXAMPLE 1

5'-[3-(2-Chloroethylureido)]-5'-deoxythymidine (3)

To a solution of 5'-amino-5'-deoxythymidine, prepared by the procedure of Horwitz et al, J. Org. Chem., 27, 3045 (1962), (2, 1.21 g, 5.02 mmol) in 60 ml of methanolwater (2:1 v/v) at 0° was added slowly 2-chloroethyl isocyanate (0.58 g, 5.52 mmol). Upon addition of the isocyanate, white crystals precipitated out immediately. The reaction mixture was stirred at 0° for 1 h and the product was collected by filtration, washed with cold methanol, ether, and dried, to yield 1.65 g (94%) of analytical sample: mp 215°–216° dec; TLC: R$_f$ 0.46. Anal. (C$_{13}$H$_{19}$ClN$_4$O$_5$) C, H, N.

EXAMPLE 2

5'-[3-(2-Chloroethyl)-nitrosoureido]-5'-deoxythymidine (5)

To an ice-cooled solution of 3 (1.16 g, 3.35 mmol) in 50 ml of 50% aqueous acetic acid, sodium nitrite (0.31 g, 4.55 mmol) was added slowly. The reaction mixture was stirred at 0° for 6 h, treated with AG50W-X8 (H$^+$) ion-exchange resin (5 g, Bio-Rad Lab.), and then stirred for another hour at the same temperature. After removal of the resin by filtration, the filtrate was evaporated to dryness in vacuo below 35°. The residue was crystallized twice from methanol to give 0.84 g (67%) of fine pale yellow crystals: mp 147°–148° dec; TLC: R$_f$ 0.69 (CHCl$_3$-EtOH v/v 4:1); uv$\lambda_{max}^{EtOH}$ 265 nm (ε13,180); uv$\lambda_{min}^{EtOH}$ 234 nm. The NMR spectrum of this sample indicated that it is a mixture of two isomers (5a and 5b) in a ratio of ~40% and 60%. Anal. (C$_{13}$H$_{18}$ClN$_5$O$_6$) C, H, N.

Attempts to separate 5a and 5b from the isomeric mixture by TLC using various solvent systems (i.e. CHCl$_3$-EtOH, EtOAc-EtOH, n-BuOH-AcOH-H$_2$O) were unsuccessful. However isomer 5b was isolated from the mother liquor and purified by repeated recrystallization from EtOH: mp160°–161°; TLC: R$_f$ 0.69 (CHCl$_3$-EtOH v/v 4:1); uv$\lambda_{max}^{EtOH}$ 265 nm (ε12,850); uv$\lambda_{min}^{EtOH}$ 234 nm. Anal. (C$_{13}$H$_{18}$ClN$_5$O$_6$) C, H, N.

EXAMPLE 3

5'-(3-Methylureido)-5'-deoxythymidine (4)

To a solution of 5'-amino-5'-deoxythymidine (2, 2.40 g, 9.95 mmol) in methanol-water (2.5:1, v/v) at 0° was added methyl isocyanate (0.63 g, 10.95 mmol). The reaction mixture was kept at 0° with stirring for 1 h, allowed to warm up to room temperature, and then clarified by filtration. The filtrate was evaporated to dryness under reduced pressure at a temperature not exceeding 35°, and the residue was then crystallized from methanol at 3° overnight to give 2.14 g (72%) of white fine needles: mp 238–239°. Anal. (C$_{12}$H$_{18}$N$_4$O$_5$) C, H, N.

EXAMPLE 4

5'-(3-Methyl-3-nitrosoureido)-5'-deoxythymidine (6)

To a solution of 4 (1.00 g, 3.35 mmol) in 50% aqueous acetic acid at 0°, sodium nitrite (0.31 g, 4.55 mmol) was added slowly. The reaction mixture was kept at 0° with stirring for 3 h, during which time crystals started to precipitate out. The product was collected by filtration, washed with water, cooled methanol, ether, and dried. The filtrate was concentrated and an additional fraction of crystals was obtained. The combined product was recrystallized from methanol to yield 0.77 g (70%) of white fine needles: mp 159°–160° dec.: uv$\lambda_{max}^{EtOH}$ 264 nm (ε11,000); uv$\lambda_{min}^{EtOH}$ 235 nm. Anal. (C$_{12}$H$_{17}$N$_5$O$_6$) C, H, N.

EXAMPLE 5

3'-Amino-3'-deoxythymidine (7)

A solution of 3'-azido-3'-deoxythymidine, prepared by the procedure of Horwitz et al, J. Org. Chem., 29, 2076 (1964) (6.10 g, 22.83 mmol) in 100 ml of ethanol was hydrogenated under 50 psi of hydrogen pressure at room temperature for 5 h in the presence of 10% palladium on charcoal (0.7 g). The catalyst was removed by filtration and the filtrate was evaporated to dryness.

The residue was dissolved in a minimum amount of water and the pH of the aqueous solution was adjusted to 3 with hydrochloric acid. The solution was then applied directly to a column (2 × 24 cm) of AG50W-X8 (H+) ion-exchange resin, washed thoroughly with water (2 liters) and the adsorbed product was eluted with 200 ml of 1n NH$_4$OH solution. The solvent was evaporated under reduced pressure and the esidue was crystallized from ethanol to afford 3.69 g (67%) of product: mp 160–161°, uv$\lambda_{max}$0.1N HCl 266 nm ($\epsilon$9,190); uv$\lambda_{min}$0.1N HCl 234 nm ($\epsilon$2,250); uv$\lambda_{max}$0.1N NaOH 268 nm ($\epsilon$7,170); uv$\lambda_{min}$0.1N NaOH 246 nm ($\epsilon$4,240). [Lit.: uv$\lambda_{max}$0.1N HCl 265 nm ($\epsilon$9,400); uv$\lambda_{min}$0.1N HCl 233 nm ($\epsilon$2,300); uv$\lambda_{max}$0.1N NaOH 266.5 nm ($\epsilon$7,400); uv$\lambda_{min}$0.1N NaOH 244 nm ($\epsilon$4,400).]

EXAMPLE 6

3'-[3-(2-Chloroethylureido)]-3'-deoxythymidine (8)

To a solution of 7 (1.69 g, 7.00 mmol) in 35 ml of methanol at 0°, 2-chloroethyl isocyanate (0.89 g, 8.40 mmol) was added slowly. After completion of the addition, the reaction mixture was stirred at room temperature for 3 h. The solvent was evaporated in vacuo to give a residue which was used for next step without further purification.

EXAMPLE 7

3'-[3-(2-Chloroethyl)-3-nitrosoureidol]-3'-deoxythymidine (10)

To a solution of 8 (as a residue) in 20 ml of 50% aqueous acetic acid, sodium nitrite (0.97 g, 14.0 mmol) was added slowly. The reaction mixture was stirred at 0° for 5 h and then treated with AG50W-X8 (H+) ion-exchange resin (6.5 g, Bio-Rad Lab.) to remove Na+. The resin containing mixture was stirred for an additional 30 min and then filtered. The filtrate was evaporated to dryness under reduced pressure below 35°, and the residue was dissolved in a minimum amount of ethanol. Upon the addition of ether to the alcoholic solution, a pale yellow solid precipitated out. The solid was collected by filtration, dried, to give 1.83 g of crude product which was dissolved in a minimum amount of ethanol-DMF (2:1 v/v) and applied directly to 12 Analtech silica gel GF plates. The plates were developed with CHCl$_3$-EtOH (3:1 v/v) as the solvent system. The desired pale yellow band (R$_f$0.7) was scratched off the plates, and the product was extracted with CHCl$_3$-EtOH (1:1 v/v, 3 × 150 ml). The silica gel was removed by filtration, and then the filtrate was concentrated to a small volume (~20 ml). Ether was added to the solution and pale yellow crystals precipitated out. The product was isolated by filtration, washed with ether, and dried, to yield 1.12 g (43% based on 7) of analytical pure sample. The compound effervesced above 95° and decomposed at 120°: uv$\lambda_{max}^{EtOH}$ 266 nm ($\epsilon$12,350); uv$\lambda_{min}^{EtOH}$ 235 nm. Anal. (C$_{13}$H$_{18}$ClN$_5$O$_6$) C, H, N.

EXAMPLE 8

3'-(3-Methylureido)-3'-deoxythymidine (9)

To a solution of 7 (0.48 g, 2.00 mmol) in 15 ml of methanol, methyl isocyanate (0.13 g, 2.20 mmol) was added slowly. The solution was stirred at 0° for 1 h, during which period, white crystals precipitated out. The product was collected by filtration, washed with cooled methanol, and dried, to give 0.54 g (90%). The compound softened at 114° and effervesced at 120°; TLC: R$_f$0.38. Anal. (C$_{12}$H$_{18}$N$_4$O$_5$) C, H, N.

EXAMPLE 9

3'-(3-Methyl-3-nitrosoureido)-3'-deoxythymidine (11)

To an ice-cooled solution of 9 (0.48 g, 1.61 mmol) in 15 ml of 80% aqueous acetic acid, sodium nitrite (0.15 g, 2.18 mmol) was added slowly. The reaction mixture was stirred at 0° for 5 hr, and then treated with AG50W-X8 (H+) *ion-exchange resin* (3 g, Bio-Rad Lab.). The mixture was stirred for another 30 min and then filtered. The filrate was evaporated to dryness in vacuo below 35° to yield a residue which was crystallized from ethanol. The product was isolated by filtration, washed with cooled ethanol, ether, and dried, to afford 0.28 g (53%) of pale yellow crystals: mp 159° (dec); TLC: R$_f$ 0.72: uv$\lambda_{max}^{EtOH}$ 265 nm ($\epsilon$12,000); uv$\lambda_{min}^{EtOH}$ 238 nm; ir (KBr) $\nu$max 1528 cm$^{-1}$ with shoulder at 1510 cm$^{-1}$ (N-H bending and C-NO stretching).

The following Table 2 shows the results of elemental analysis of certain of the compounds obtained in the examples:

TABLE 2

Analyses Appendix

| Compd | Formula | Calcd C | H | N | Found C | H | N |
|---|---|---|---|---|---|---|---|
| 3 | C$_{13}$H$_{19}$ClN$_4$O$_5$ | 45.03 | 5.52 | 16.16 | 44.68 | 5.68 | 16.08 |
| 4 | C$_{12}$H$_{18}$N$_4$O$_5$ | 48.32 | 6.08 | 18.78 | 47.99 | 6.19 | 18.77 |
| 5* | C$_{13}$H$_{18}$ClN$_5$O$_6$ | 41.55 | 4.83 | 18.64 | 41.81 | 4.81 | 18.55 |
| 5b | C$_{13}$H$_{18}$ClN$_5$O$_6$ | 41.55 | 4.83 | 18.64 | 41.72 | 4.74 | 18.39 |
| 6 | C$_{12}$H$_{17}$N$_5$O$_6$ | 44.04 | 5.24 | 21.40 | 44.30 | 5.44 | 21.36 |
| 9 | C$_{12}$H$_{18}$N$_4$O$_5$ | 48.32 | 6.08 | 18.78 | 48.52 | 6.19 | 18.33 |
| 10 | C$_{13}$H$_{18}$ClN$_5$O$_6$ | 41.55 | 4.83 | 18.64 | 41.65 | 5.01 | 18.36 |

*Sample 5 is an isomeric mixture of ~40% 5a and 60% 5b (estimated by NMR integral ratios).

EXAMPLE 10

Culture Study with L1210

The effect of the compounds on the growth of L1210 cells in vitro was used as a measure of cytotoxicity. Suspension cultures were grown in Fischer's media supplemented with 10% horse serum at 37°. 72 Hours after addition of the nitrosoureas, cell numbers were determined in two independent samples, in duplicate, using a Coulter counter, for each concentration tested. ED$_{50}$ values were estimated from dose-response curves compiled from at least three separate experiments and represent the drug concentration needed to inhibit cell growth by 50%. It was found that under conditions in which BCNU [1,3-Bis(2-chloroethyl)-1-nitrosourea], a clinically useful drug, required a concentration of 4 $\mu$M to inhibit the replication of L1210 cells, compound 11 required only 1 $\mu$M to achieve the same degree of inhibition.

EXAMPLE 11

In Vivo Study with Mice

Two groups of CDF$_1$ mice were inoculated with 1 × 10$^5$ L1210 cells/animal intraperitoneally. Two days later, one group of six mice received a single intraperitoneal injection (150 mg/Kg) of compound 5 (5'-[3-(2-chloroethyl)-3-nitrosoureido]-5'-deoxythymidine) and the control group was administered an equal volume of vehicle.

The median life span of the control group was 9.5 days, and there were no survivors. In the drug treated group, 2/6 animals survived more than 60 days and there was 211% increase in life span of the dying animals. The results indicate that a single injection of compound 5 produced approximately a 5 log tumor cell kill.

EXAMPLE 12

Inhibition Study in Cultures

Effect of Deoxycytidine on the Cytotoxicity of Compound 11.

| Compound 11 | Deoxycytidine | Percent Inhibition |
|---|---|---|
| None | None | 0% |
| 5 µM | — | 100% |
| 5 µM | 5 µM | 58% |
| 5 µM | 25 µM | 26% |
| 5 µM | 125 µM | 0% |

Suspension cultures of L1210 cells were grown in Fischer's media supplemented with 10% horse serum at 37°. The concentrations of the nitrosourea analog (compound 11) and the reversal agent (deoxycytidine) shown in the above table were added. The number of cells were determined in two independent samples, in duplicate, using a Coulter counter for each concentration evaluated. The cell number was determined daily and the percent inhibition in the above table was that after 72 hours incubation.

What is claimed is:

1. A compound selected from the group consisting of:

5'-[3-(2-chloroethyl)-nitrosoureido]-5'-deoxythymidine,
5'-(3-methyl-3-nitrosoureido)-5'-deoxythymidine,
3'-[3-(2-chloroethyl)-3-nitrosoureido]-3'-deoxythymidine, and
3'-(3-methyl-3-nitrosoureido)-3'-deoxythymidine.

2. A compound selected from the group consisting of:

5'-[3-(2-chloroethylureido)]-5'-deoxythymidine,
5'-(3-methylureido)-5'-deoxythymidine,
3'-[3-(2-chloroethylureido)]-3'-deoxythymidine, and
3'-(3-methylureido)-3'-deoxythymidine.

3. 5'-[3-(2-chloroethyl)-nitrosoureido]-5'-deoxythymidine.

4. 5'-(3-methyl-3-nitrosoureido)-5'-deoxythymidine.

5. 3'-[3-(2-chloroethyl)-3-nitrosoureido]-3'-deoxythymidine.

6. 3'-(3-methyl-3-nitrosoureido)-3'-deoxythymidine.

7. A pharmaceutical composition containing a compound selected from the group consisting of:

5'-[3-(2-chloroethyl)-nitrosoureido]-5'-deoxythymidine,
5'-(3-methyl-3-nitrosoureido)-5'-deoxythymidine,
3'-[3-(2-chloroethyl)-3-nitrosoureido]-3'-deoxythymidine,
3'-(3-methyl-3-nitrosoureido)-3'-deoxythymidine, and a pharmaceutically acceptable carrier.

8. 5'-[3-(2-chloroethylureido)]-5'-deoxythymidine.
5'-(3-methylureido)-5'-deoxythymidine.

9. 5'-(3-methylureido)-5'-deoxythymidine.

10. 3'-[3-(2-chloroethylureido)]-3'-deoxythymidine.

11. 3'-(3-methylureido)-3'-deoxythymidine.

* * * * *